(12) United States Patent
Peine (10) Patent No.: US 11,717,363 B2
(45) Date of Patent: Aug. 8, 2023

(54) HIGH PRECISION INSTRUMENT CONTROL MODE FOR ROBOTIC SURGICAL SYSTEMS

(71) Applicant: Covidien LP, Mansfield, MA (US)

(72) Inventor: William Peine, Ashland, MA (US)

(73) Assignee: COVIDIEN LP, Mansfield, MA (US)

( * ) Notice: Subject to any disclaimer, the term of this patent is extended or adjusted under 35 U.S.C. 154(b) by 675 days.

(21) Appl. No.: 16/644,875

(22) PCT Filed: Sep. 6, 2018

(86) PCT No.: PCT/US2018/049634
§ 371 (c)(1),
(2) Date: Mar. 5, 2020

(87) PCT Pub. No.: WO2019/051005
PCT Pub. Date: Mar. 14, 2019

(65) Prior Publication Data
US 2020/0281674 A1   Sep. 10, 2020

Related U.S. Application Data

(60) Provisional application No. 62/556,100, filed on Sep. 8, 2017.

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/77* (2016.02); *A61B 90/361* (2016.02);
(Continued)

(58) Field of Classification Search
USPC .................................................. 700/245–264
See application file for complete search history.

(56) References Cited

U.S. PATENT DOCUMENTS

| 5,552,807 A | 9/1996 | Hayes et al. |
| 5,554,894 A | 9/1996 | Sepielli |

(Continued)

FOREIGN PATENT DOCUMENTS

| CN | 106455916 A | 2/2017 |
| CN | 106456260 A | 2/2017 |

(Continued)

OTHER PUBLICATIONS

Partial Supplementary European Search Report dated May 4, 2021 corresponding to counterpart Patent Application EP 18853735.1.

(Continued)

*Primary Examiner* — Jonathan L Sample
(74) *Attorney, Agent, or Firm* — Carter, DeLuca & Farrell, LLP (57) ABSTRACT

A foot pedal for a robotic surgical system includes a base plate, a foot plate, a first biasing member, and a second biasing member. The foot plate is pivotally coupled to the base plate and has uncompressed, partially compressed, and fully compressed positions. The first biasing member is configured to urge the foot plate towards the uncompressed position when the foot plate is between the fully compressed and uncompressed positions. The second biasing member is configured to urge the foot plate towards the uncompressed position when the foot plate is between the fully compressed and partially compressed positions. Methods for using the foot pedal to control a tool and a camera of a surgical robot are also disclosed.

23 Claims, 4 Drawing Sheets

(51) Int. Cl.
  *A61B 90/00* (2016.01)
  *A61B 17/00* (2006.01)
(52) U.S. Cl.
  CPC .............. *A61B 2017/00977* (2013.01); *A61B 2034/742* (2016.02); *A61B 2090/373* (2016.02)

(56) References Cited

U.S. PATENT DOCUMENTS

| | | | |
|---|---|---|---|
| 7,074,179 B2* | 7/2006 | Wang | A61B 34/77 |
| | | | 414/2 |
| 7,193,169 B2 | 3/2007 | Mezhinsky et al. | |
| 7,781,941 B2* | 8/2010 | Horvath | H01H 21/26 |
| | | | 310/319 |
| 8,828,023 B2 | 9/2014 | Neff et al. | |
| 9,333,042 B2* | 5/2016 | Diolaiti | A61B 34/72 |
| 9,375,288 B2* | 6/2016 | Robinson | A61B 34/76 |
| 10,368,955 B2* | 8/2019 | Cone | G05G 1/305 |
| 2003/0047434 A1* | 3/2003 | Hanson | G05G 1/30 |
| | | | 200/86.5 |
| 2005/0234433 A1* | 10/2005 | Wang | B25J 9/1689 |
| | | | 606/1 |
| 2007/0089557 A1 | 4/2007 | Solomon et al. | |
| 2009/0216189 A1 | 8/2009 | Gasser et al. | |
| 2010/0161129 A1 | 6/2010 | Costa et al. | |
| 2010/0274087 A1* | 10/2010 | Diolaiti | A61B 90/361 |
| | | | 700/275 |
| 2011/0118748 A1* | 5/2011 | Itkowitz | A61B 34/30 |
| | | | 606/130 |
| 2011/0238079 A1* | 9/2011 | Hannaford | A61B 34/76 |
| | | | 606/130 |
| 2014/0081455 A1* | 3/2014 | Goldberg | A61B 90/98 |
| | | | 700/250 |
| 2014/0378986 A1 | 12/2014 | Eastman et al. | |
| 2015/0051607 A1* | 2/2015 | Hajishah | G05G 1/445 |
| | | | 341/20 |
| 2015/0141755 A1 | 5/2015 | Tesar | |
| 2016/0098943 A1* | 4/2016 | Valeev | G09B 23/30 |
| | | | 434/267 |
| 2017/0136159 A1 | 5/2017 | Mallough | |
| 2018/0083621 A1* | 3/2018 | Ekvall | H03K 17/975 |
| 2018/0132948 A1* | 5/2018 | Mercado | A61B 34/30 |
| 2018/0221100 A1* | 8/2018 | Berry | A61B 34/37 |
| 2018/0280099 A1* | 10/2018 | Cone | B25J 13/04 |
| 2019/0350757 A1* | 11/2019 | Charles | A61F 9/00736 |
| 2020/0375673 A1 | 12/2020 | Peine | |

FOREIGN PATENT DOCUMENTS

| | | |
|---|---|---|
| JP | 2017525401 A | 9/2017 |
| WO | 2015175278 A1 | 11/2015 |
| WO | 2018217522 A1 | 11/2018 |
| WO | 2018217524 A2 | 11/2018 |
| WO | 2018217527 A1 | 11/2018 |
| WO | 2020060793 A1 | 3/2020 |

OTHER PUBLICATIONS

Extended European Search Report dated Sep. 8, 2021 corresponding to counterpart Patent Application EP 18853735.1.
International Search Report dated Dec. 19, 2018 and Written Opinion completed Dec. 19, 2018 corresponding to counterpart Int'l Patent Application PCT/US2018/049634.
U.S. Appl. No. 62/510,502, filed May 24, 2017, entitled "Pedal Control for Robotic Surgical Systems".
Chinese First Office Action dated Aug. 25, 2022 corresponding to counterpart Patent Application CN 201880058146.8.
Indian Office Action dated Apr. 11, 2022 corresponding to counterpart Patent Application IN 202017009360.
Japanese Office Action dated Aug. 3, 2022 corresponding to counterpart Patent Application JP 2020 513707.

* cited by examiner

HIGH PRECISION INSTRUMENT CONTROL MODE FOR ROBOTIC SURGICAL SYSTEMS

CROSS-REFERENCE TO RELATED APPLICATIONS

This application is a U.S. National Stage Application filed under 35 U.S.C. § 371(a) of International Patent Application Serial No. PCT/US2018/049634, filed Sep. 6, 2018, which claims the benefit of and priority to U.S. Provisional Patent Application Ser. No. 62/556,100, filed Sep. 8, 2017, the entire disclosure of which is incorporated by reference herein.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector of a surgical instrument that acts on a patient. The user interface includes an input controller or handle that is moveable by the surgeon to control the robotic surgical system.

Robotic surgical systems typically use a scaling factor to scale down the motions of the hands of a surgeon to determine the desired position of the end effector within the patient so that the surgeon can more precisely move the end effector inside the patient.

During a surgical procedure, it may be desirable to increase the precision of movements of the end effector within the patient. Typically, to adjust the scaling or increase the precision of movements of the end effector, a surgeon must release an input handle to adjust the scaling of movements of the end effector.

There is a need for apparatus and methods for adjusting scaling of robotic surgical systems to selectively increase precision of movements of an end effector without requiring a surgeon to release an input handle during a surgical procedure.

SUMMARY

In an aspect of the present disclosure, a foot pedal for a robotic surgical system includes a base plate, a foot plate, a first biasing member, and a second biasing member. The foot plate is pivotally coupled to the base plate and has uncompressed, partially compressed, and fully compressed positions. The first biasing member is configured to urge the foot plate towards the uncompressed position when the foot plate is between the fully compressed and uncompressed positions. The second biasing member is configured to urge the foot plate towards the uncompressed position when the foot plate is between the fully compressed and partially compressed positions.

In aspects, the second biasing member is offset from the first biasing member. The second biasing member may be secured to the base plate and may engage the foot plate as the foot plate reaches the partially compressed position.

In another aspect of the present disclosure, a robotic surgical system includes a surgical robot and a user console. The surgical robot includes a tool and a camera. The user console is in communication with the surgical robot and includes an input handle and a foot pedal. The foot pedal includes a base plate and a foot plate that is pivotally coupled to the base plate. The foot plate has an uncompressed position in which movement of the input handle is scaled to movement of the tool by a first scaling factor, a first compressed position in which movement of the input handle is scaled to movement of the tool by a second scaling factor that is different from the first scaling factor, and a fully compressed position in which movement of the input handle is scaled to movement of the camera.

In aspects, the foot pedal includes a first biasing member that is configured to urge the foot plate towards the uncompressed position when the foot plate is between the fully compressed and uncompressed positions. The foot pedal may include a second biasing member that is configured to urge the foot plate towards the uncompressed position when the foot plate is between the fully compressed and partially compressed positions.

In some aspects, the camera remains stationary in response to movement of the input handle when the foot pedal is between the uncompressed and first compressed positions. Between the first compressed and fully compressed positions the input handle may be in a hold mode such that the user console applies a force to the input handle to at least one of maintain or move the input handle to a hold pose. The hold pose may defined by a pose of the input handle when the foot pedal is compressed to the first compressed position. The hold pose may be redefined when the foot pedal is moved from the first compressed position towards the uncompressed position and returned to the first compressed position. The camera may be throttled based on a distance the input handle is moved from the hold pose when the foot pedal is in the fully compressed position.

In certain aspects, the foot pedal has a second compressed position between the first compressed and fully compressed positions. Movement of the input handle may move the camera when the foot pedal is between the second compressed and fully compressed positions. The camera may remain stationary in response to movement of the input handle when the foot pedal is between the uncompressed and second compressed positions. Movement of the input handle may be scaled to movement of the tool by a third scaling factor that is different from the first and second scaling factors when the foot pedal is in the second compressed position. Movement of the input handle may be scaled to movement of the tool by a fourth scaling factor that is different from the first, second, and third scaling factors when the foot pedal is in the fully compressed position.

In particular aspects, the first scaling factor is about 3 and the second scaling factor is about 10. The third scaling factor may be in a range of about 11 to about 500 and the fourth scaling factor may be in a range of about 100 to about 1000.

In another aspect of the present disclosure, a method of controlling a surgical robot with a processing unit of a robotic surgical system includes receiving a position of a foot pedal of a user console of the robotic surgical system, receiving an input signal from the user console, transmitting control signals to the surgical robot to move at least one of a tool of the surgical robot or a camera of the surgical robot in response to receiving the input signal. The input signal includes movement of an input handle of the user console. The processing unit scales the input signal to movement of the tool by a first scaling factor when the foot pedal is in an uncompressed position, scales the input signal to movement of the tool by a second scaling factor that is different from the first scaling factor when the foot pedal is in a first compressed position, and scale the input signal to movement of the camera when the foot pedal is in a fully compressed position.

In aspects, the processing unit maintains the position of the camera when the foot pedal is between the uncompressed position and a second compressed position that is between the first compressed and fully compressed positions. Transmitting control signals to the surgical robot may include transmitting control signals to throttle movement of the camera when the foot pedal is between the second compressed and fully compressed positions.

Further details and aspects of exemplary embodiments of the present disclosure are described in more detail below with reference to the appended figures.

BRIEF DESCRIPTION OF THE DRAWINGS

Various aspects of the present disclosure are described herein below with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician. In addition, as used herein the term "pose" is understood to mean a position and orientation of an object in space. Further, as used herein the term "neutral" is understood to mean non-scaled.

This disclosure generally relates to a foot pedal for use with a robotic surgical system that allows a clinician to vary scaling of movements of an input handle of a user console to movements of a tool of a surgical robot and to vary scaling of movements of the input handle to movements of a camera. The foot pedal has an uncompressed position in which movement of the input handle is scaled by a first scaling factor to movement of the tool, a first compressed position in which movement of the input handle is scaled by a second scaling factor to movement of the tool, and a fully compressed position in which movement of the input handle effects movement of the camera.

Figure 1:
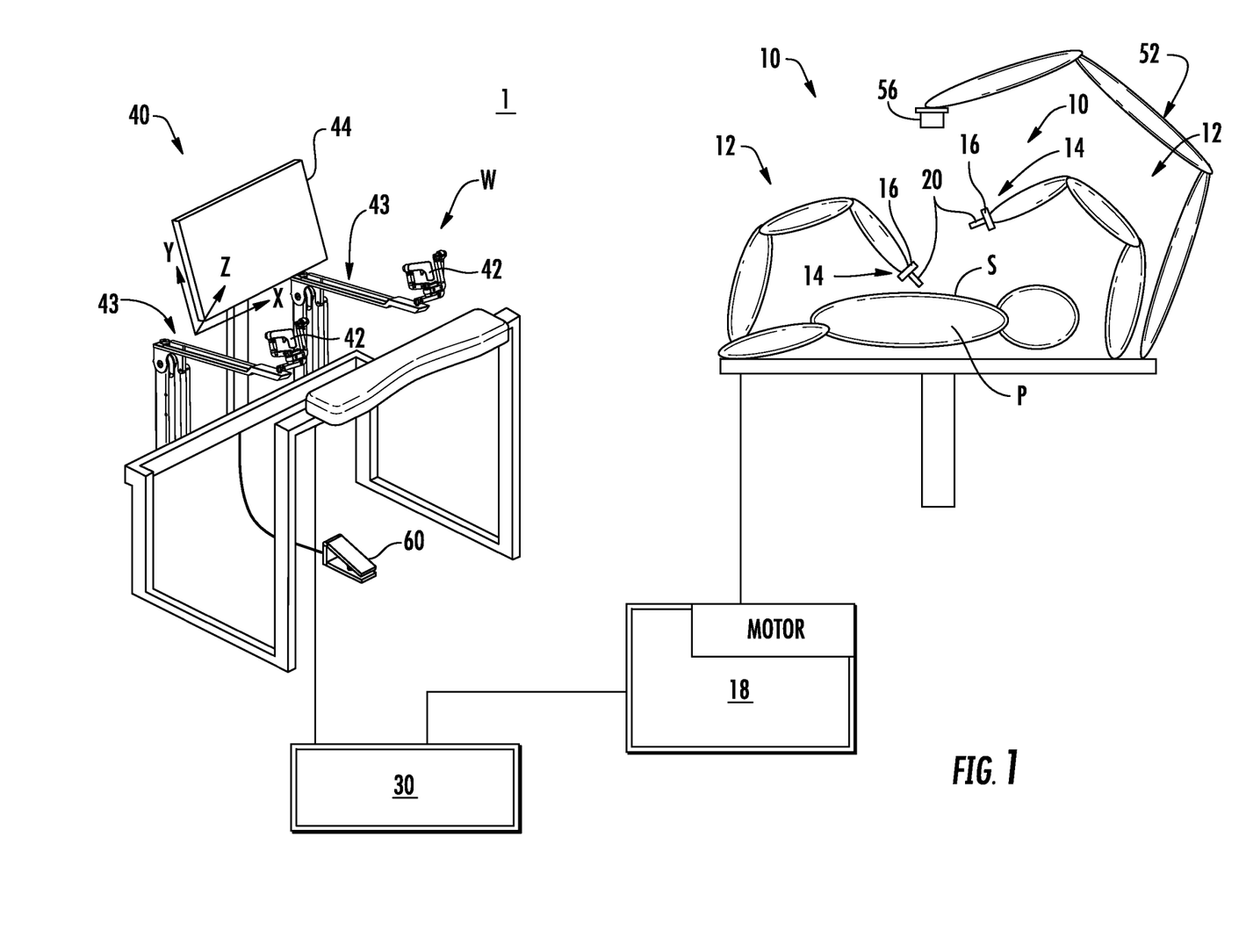
FIG. 1 is a schematic illustration of a user console and a surgical robot of a robotic surgical system in accordance with the present disclosure.

Referring to FIG. 1, a robotic surgical system 1 in accordance with the present disclosure is shown generally as a surgical robot 10, a processing unit 30, and a user console 40.

The surgical robot 10 generally includes linkages 12 and a robot base 18. The linkages 12 moveably support an end effector or tool 20 which is configured to act on tissue. The linkages 12 may be in the form of arms each having an end 14 that supports the end effector or tool 20 which is configured to act on tissue. In addition, the ends 14 of the linkages 12 may include an imaging device 16 for imaging a surgical site "S". The user console 40 is in communication with robot base 18 through the processing unit 30.

The user console 40 includes a display device 44 which is configured to display three-dimensional images. The display device 44 displays three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user console 40 also includes input handles 42 which are supported on control arms 43 which allow a clinician to manipulate the surgical robot 10 (e.g., move the linkages 12, the ends 14 of the linkages 12, and/or the tools 20). Each of the input handles 42 is in communication with the processing unit 30 to transmit control signals thereto and to receive feedback signals therefrom. Additionally or alternatively, each of the input handles 42 may include input devices (not explicitly shown) which allow the surgeon to manipulate (e.g., clamp, grasp, fire, open, close, rotate, thrust, slice, etc.) the tools 20 supported at the ends 14 of the linkages 12.

Each of the input handles 42 is moveable through a predefined workspace to move the ends 14 of the linkages 12, e.g., tools 20, within a surgical site "S". The three-dimensional images on the display device 44 are orientated such that the movement of the input handles 42 moves the ends 14 of the linkages 12 as viewed on the display device 44. The three-dimensional images remain stationary while movement of the input handles 42 is scaled to movement of the ends 14 of the linkages 12 within the three-dimensional images. To maintain an orientation of the three-dimensional images, kinematic mapping of the input handles 42 is based on a camera orientation relative to an orientation of the ends 14 of the linkages 12. The orientation of the three-dimensional images on the display device 44 may be mirrored or rotated relative to the view captured by the imaging devices 16, 56. In addition, the size of the three-dimensional images on the display device 44 may be scaled to be larger or smaller than the actual structures of the surgical site permitting a clinician to have a better view of structures within the surgical site "S". As the input handles 42 are moved, the tools 20 are moved within the surgical site "S" as detailed below. Movement of the tools 20 may also include movement of the ends 14 of the linkages 12 which support the tools 20.

For a detailed discussion of the construction and operation of a robotic surgical system 1, reference may be made to U.S. Pat. No. 8,828,023, the entire contents of which are incorporated herein by reference.

The user console 40 further includes a foot pedal 60 that can be used to control various aspects of the robotic surgical system 1. For example, the foot pedal 60 may be selectively associated with an input handle, e.g., input handle 42, to actuate a tool 20 associated with the respective input handle. Additionally or alternatively, the foot pedal 60 may be associated with a camera, e.g., camera 56, to move the camera about the surgical site "5". For a detailed discussion of suitable foot pedals, reference may be made to U.S. Provisional Patent Application Ser. No. 62/510,502, filed May 24, 2017, entitled "PEDAL CONTROL FOR ROBOTIC SURGICAL SYSTEMS," the entire contents of which are hereby incorporated by reference.

With reference to FIGS. 2A-2D, the foot pedal 60 includes a base plate 62 defining a plane, a foot plate 64 defining a plane, and a first biasing member 66. The foot plate 64 is pivotally coupled to the base plate 62 about a pivot 63 to define an angle θ between the respective planes thereof. The foot plate 64 is pivotable between an initial or uncompressed position (FIG. 2A) in which the angle θ is about 90°, a first depressed position (FIG. 2B) in which the angle θ is about 80°, a second depressed position (FIG. 2C) in which the angle θ is about 70°, and a fully depressed position (FIG. 2D) in which the angle θ is about 65°. It is envisioned that the angle θ at each of the above positions may vary from about 30° to about 110°.

The first biasing member 66 is configured to urge the foot plate 64 towards the uncompressed position. The first biasing member 66 is substantially in contact with the foot plate 64 and the base plate 62 between the uncompressed and fully compressed positions to urge the foot plate 64 away from the base plate 62 with a first biasing force. The first biasing member 66 may have a constant or progressive spring force as the foot plate 64 is compressed. As shown, the first biasing member 66 is a compression spring positioned between the foot plate 64 and the base plate 62. However, the first biasing member 66 may be a torsion spring disposed about the pivot 63.

The foot pedal 60 may also have a second biasing member 68 that is configured to urge the foot plate 64 away from the base plate 62. The second biasing member 68 is configured to apply a second biasing force to the foot plate 64 when the foot plate 64 reaches a predetermined position between the uncompressed and fully compressed positions. As shown, the second biasing member 68 is positioned to apply the second biasing force when the foot plate 64 is between the second compressed position and the fully compressed position. In some embodiments, the second biasing member 68 is not in contact with the foot plate 64 between the uncompressed position and the second compressed position. In addition, the second biasing member 68 may be attached to the foot plate 64 to selectively engage the base plate 62. As shown, the second biasing member 68 is a compression spring that is offset from the first biasing member 66. However, the second biasing member 68 may be coaxial with the first biasing member 66 such that the second biasing member 68 is positioned within or surrounding the first biasing member 66. Further, the second biasing member 68 may be a torsion spring disposed about the pivot 63. The second biasing member 68 may have a constant or progressive spring constant as the second biasing member 68 is compressed.

In some embodiments, the foot pedal 60 includes additional biasing members which are similar to the first and second biasing members 66, 68 to provide discreet forces which provide feedback to a clinician engaged with the foot pedal 60 as described in greater detail below.

Figure 2A:
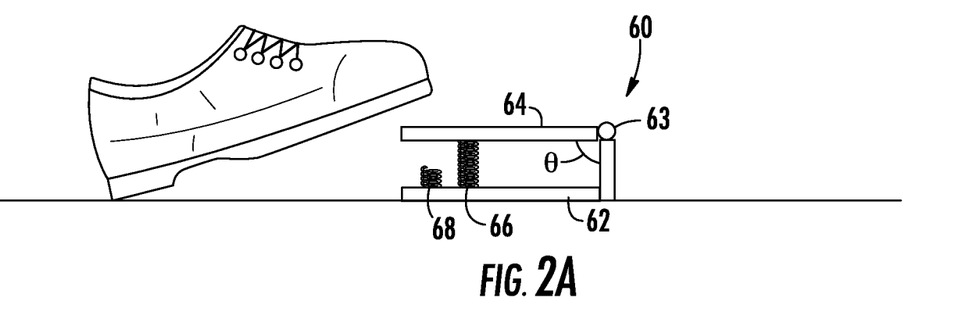
FIG. 2A is a schematic illustration of a foot pedal of the user console of FIG. 1 in an uncompressed position.
Figure 2B:
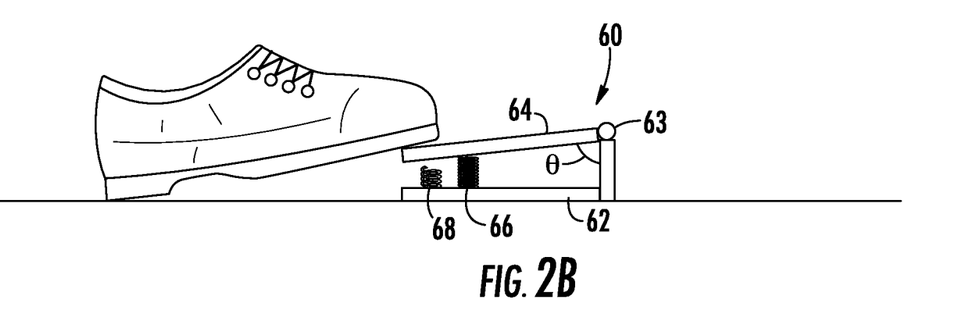
FIG. 2B is a schematic illustration of the foot pedal of FIG. 2 in a first compressed position.
Figure 2C:
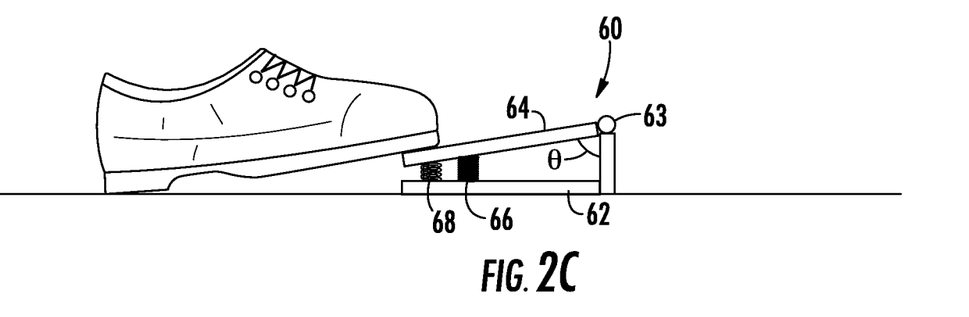
FIG. 2C is a schematic illustration of the foot pedal of FIG. 2 in a second compressed position.
Figure 2D:
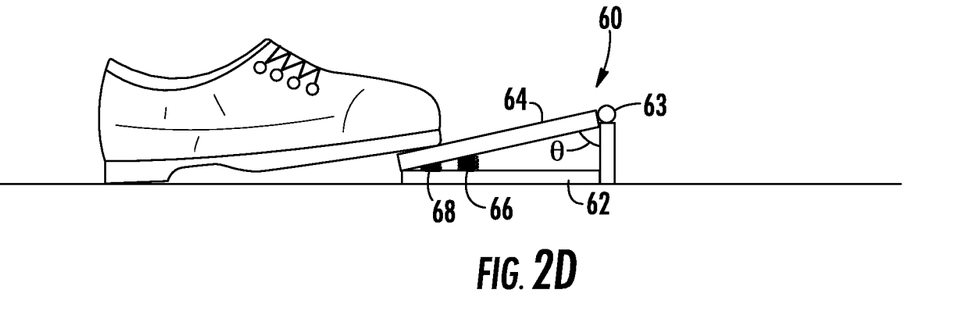
FIG. 2D is a schematic illustration of the foot pedal of FIG. 2 in a fully compressed position.
Figure 3:
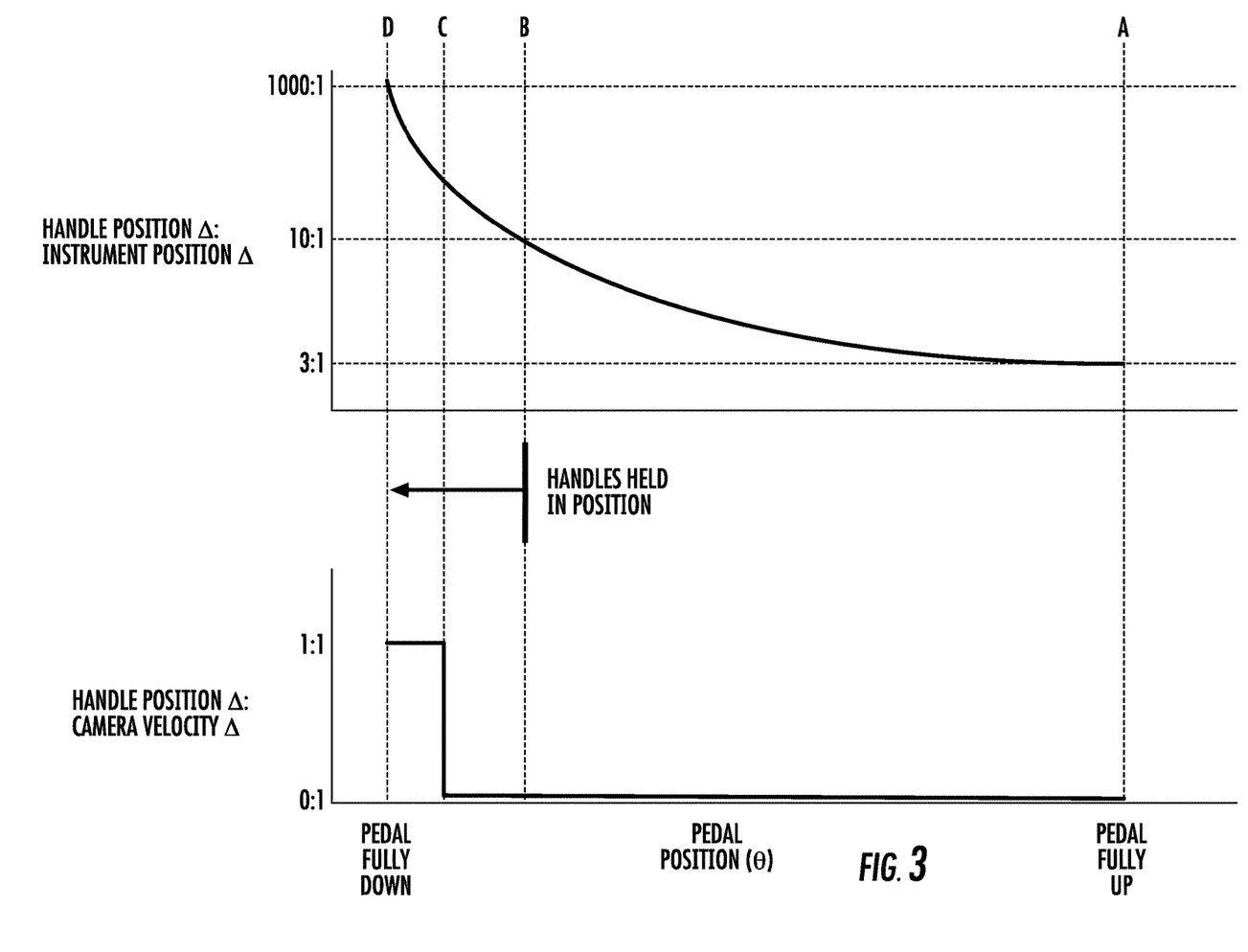
FIG. 3 are graphs illustrating a method of varying a scaling factor of an input handle of the user console of FIG. 1 to a tool of the surgical robot of FIG. 1 and a scaling factor of the input handle to a camera of the surgical robot of FIG. 1 based on a position of the foot pedal of FIG. 2.

With reference to FIGS. 1-3, the foot pedal 60 is configured to vary the scaling of the input handle 42 relative to the tool 20 and to vary a position of a camera, e.g., camera 56, in response to movement of the input handle 42. With particular reference to FIG. 3, when the foot pedal 60 is in the uncompressed position (position "A" shown in FIG. 3), movement of the input handle 42 to movement of the tool 20 is scaled down to a 3:1 ratio such that 3 inches of movement of the input handle 42 results in 1 inch of movement of the tool 20 and movement of the input handle 42 has no effect on movement of the camera 56 when the foot pedal 60 is between the uncompressed and first compressed positions.

As the foot pedal 60 is compressed towards the first compressed position (position "B" shown in FIG. 3), the scaling of movement of the input handle 42 to movement of the tool 20 varies as the foot pedal 60 is compressed from the 3:1 ratio at position "A" to a 10:1 ratio at position "B". The varying of the scaling of the ratio may be smooth as shown in FIG. 3 or may occur in discreet steps. By scaling down the movement of the input handle 42 to movement of the tool 20, the clinician may be able to more precisely control movements of the tool 20 within the surgical site "S".

When the foot pedal 60 reaches the first compressed position, e.g., position "B", the input handle 42 may enter a "hold mode". Specifically, as the foot pedal reaches the first compressed position, the input handle 42 defines a "hold pose" which is the pose of the input handle 42 when the foot pedal 60 first reaches the first compressed position. The "hold pose" is redefined when the foot pedal 60 is returned to a position between the first compressed position and the uncompressed position and then returned to the first compressed position. In the hold mode, the control arm 43 and/or input handle 42 maintain and/or return the input handle 42 to the hold pose. For example, motors (not shown) associated with the control arm 43 may apply force feedback algorithms to the input handle 42 and/or control arm 43 to maintain and/or return the input handle 42 to the hold pose.

As the foot pedal 60 is pivoted from the first compressed position to the fully compressed position, movement of the input handle 42 to movement of the tool 20 is scaled down further from the 10:1 ratio to a 1000:1 ratio such that movement of the input handle 42 effects very small movements of the tool 20. In addition, movement of the input handle 42 has no effect on movement of the camera 56 when the foot pedal 60 is between the first and second compressed positions.

When the foot pedal 60 reaches the second compressed position (position "C" as shown in FIG. 3), movement of the input handle 42 from the hold position has very little effect on movement of the tool 20 and moves the camera 56 within the surgical site "S" to adjust the view of the surgical site "S" on the display 44. Specifically, when the foot pedal 60 reaches the second compressed position, movement of the input handle 42 moves the camera 56 at a 1:1 ratio within the surgical site "S". It is contemplated that movement of the input handle 42 may be scaled to movement of the camera 56. For example, movement of the input handle 42 may be scaled to movement of the camera 56 in a similar manner to movement of the input handle 42 to movement of the tool 20 as detailed above when the foot pedal 60 is between the second and fully compressed positions. Additionally or alternatively, movement of the input handle 42 may be throttled to movement of the camera 56 such that as the input handle 42 is moved from the hold pose, the camera 56 moves in the same direction at a velocity related to the distance that the input handle 42 is moved from the hold pose until the input handle 42 is returned to the hold pose. The velocity of movement of the camera 56 may be proportionally, quadratically, exponentially, or higher order polynomial related to the distance that the input handle 42 is moved from the hold pose. In addition, as detailed above, when the foot pedal 60 is between the second compressed position and the fully compressed position, movement of the input handle 42 relative to movement of the tool 20 is at a ratio in a range of about 100:1 to about 1000:1 such that movement of the input handle 42 from the hold position has very little effect on the position of the tool 20. It is contemplated that at the second compressed position, the input handle 42 may "clutch" from movement of the tool 20 such that the tool 20 remains stationary when the pedal 60 is between the second compressed position and the fully compressed position.

As the foot pedal 60 is compressed from the uncompressed position to the fully compressed position, the foot pedal 60 may provide feedback to the clinician when each of the first compressed position, the second compressed position, and the fully compressed position are reached to indicate the change in operation of the input handle at each position. For example, as the foot pedal 60 is compressed from the uncompressed position to the first compressed position, the increase in force to continue to compress the foot pedal 60 is the first biasing force to compress the first biasing member 66. As detailed above, the spring constant of the first biasing member may be constant or may be progressive.

When the foot pedal 60 reaches the first compressed position, the input handle 42 enters the "hold mode" such that the clinician feels force feedback when moving the input handle 42 which indicates to a clinician that the first compressed position was reached. In addition, the foot pedal 60 may have a third biasing member that is engaged at the first compressed position to provide tactile feedback through the foot pedal 60 that the first compressed position was reached.

As the foot pedal 60 is compressed from the first compressed position to the second compressed position, the increase in force to continue to compress the foot pedal 60 is the first biasing force to compress the first biasing member 66. In embodiments including the third biasing member, the increase in force to continue to compress the foot pedal 60 is a sum of the first biasing force and a biasing force to compress the third biasing member. The increase in force attributed to the third biasing member may provide tactile feedback through the foot pedal 60 that the foot pedal 60 is between the first and second compressed positions.

When the foot pedal 60 reaches the second compressed position, the second biasing member 68 is engaged to apply the second biasing force to the foot pedal 60 in addition to the first biasing force applied by the first biasing member 66. The addition of the second basing force provides tactile feedback through the foot pedal 60 that the second compressed position was reached such that movement of the input handle 42 from the hold position will affect movement of the camera 56, as detailed above.

When the foot pedal 60 is compressed from the second compressed position to the fully compressed position, the increase in force to continue to compress the foot pedal 60 is the sum of the first and second biasing forces to compress the first and second biasing members 66, 68, respectively. In embodiments including the third biasing member, the increase in force to continue to compress the foot pedal 60 is a sum of the first and second basing forces and a biasing force to compress the third biasing member.

When the foot pedal 60 reaches the fully compressed position, the foot plate 64 may contact the base plate 62 such that the foot plate 64 is prevented from additional compression. It is contemplated that the base plate 62 or the foot plate 64 may include a stop member that extends from a surface of the respective plate towards the opposing plate to contact the opposing plate in the fully compressed position.

It will be appreciated that when the foot pedal 60 is released, when in any position between the uncompressed and fully compressed position, the biasing members of the foot pedal 60, e.g., first and second biasing members 66, 68, move the foot pedal to the uncompressed position.

With reference to FIGS. 1-3, a method of manipulating a tool and a camera with an input handle and a foot pedal is described in accordance with the present disclosure utilizing the robotic surgical system 1 of FIG. 1. Initially, to manipulate the tool 20, a clinician moves the input handle 42 about the workspace "W" with the foot pedal 60 in the uncompressed position. When the clinician requires additional precision for movements of the tool 20, the clinician compresses the foot pedal 60 towards the fully compressed position to scale down movements of the tool 20 in response to movements of the input handle 42. It is contemplated that the clinician may compress the foot pedal 60 to the first compressed position as shown in FIG. 2B to increase the precision of movements of the tool 20. As detailed above, when the foot pedal 60 reaches the first compressed position, the clinician may feel feedback of the input handle 42 entering the hold mode to indicate that additional compression of the foot pedal 60 may result in reaching the second compressed position and thus, movement of the camera 56. When the additional precision is no longer required, the clinician releases the foot pedal 60 to allow the foot pedal 60 to return to the uncompressed position and then continues to manipulate the input handle 42 to move the tool 20 within the surgical site "S".

At any point during the surgical procedure, when the clinician desires to move the camera 56, the clinician compresses the foot pedal 60 beyond the second compressed position. When the foot pedal 60 is beyond the second compressed position, movement of the input handle 42 from the hold pose moves the camera 56 within the surgical site "S" as detailed above. As detailed above, when the foot pedal 60 is between the second compressed position and the fully compress position, the second biasing force from compression of the second biasing member 68 provides feedback to the clinician that the foot pedal 60 is between the second and fully compressed positions. When additional movement of the camera is no longer required, the clinician releases the foot pedal 60 to allow the foot pedal 60 to return to a position between the second compressed position and the uncompressed position.

The method as detailed above may be performed as an algorithm within the processing unit 30 (FIG. 1). For example, in response to movement of the input handle 42, the user console 40 may transmit input signals to the processing unit 30. The processing unit 30 receives the input signals and generates control signals which are transmitted to the surgical robot 10 to move the tool 20 and/or the camera 56 as detailed above.

As detailed above, the foot pedal 60 allows a single input handle, e.g., input handle 42, to control movement of a tool, e.g., tool 20, and a camera, e.g., camera 56, of a surgical robot without requiring the clinician to release the input handle or divert attention away from the surgical procedure. In addition, the foot pedal 60 also allows a clinician to vary the scaling of movements of the input handle to movements of the tool. Individually or together, each of these benefits allows a clinician to have increased awareness and control of the surgical robot which may decrease the time required to perform a surgical procedure, may improve surgical outcomes, may reduce recovery time, and may reduce costs of surgical procedures.

Figure 4:
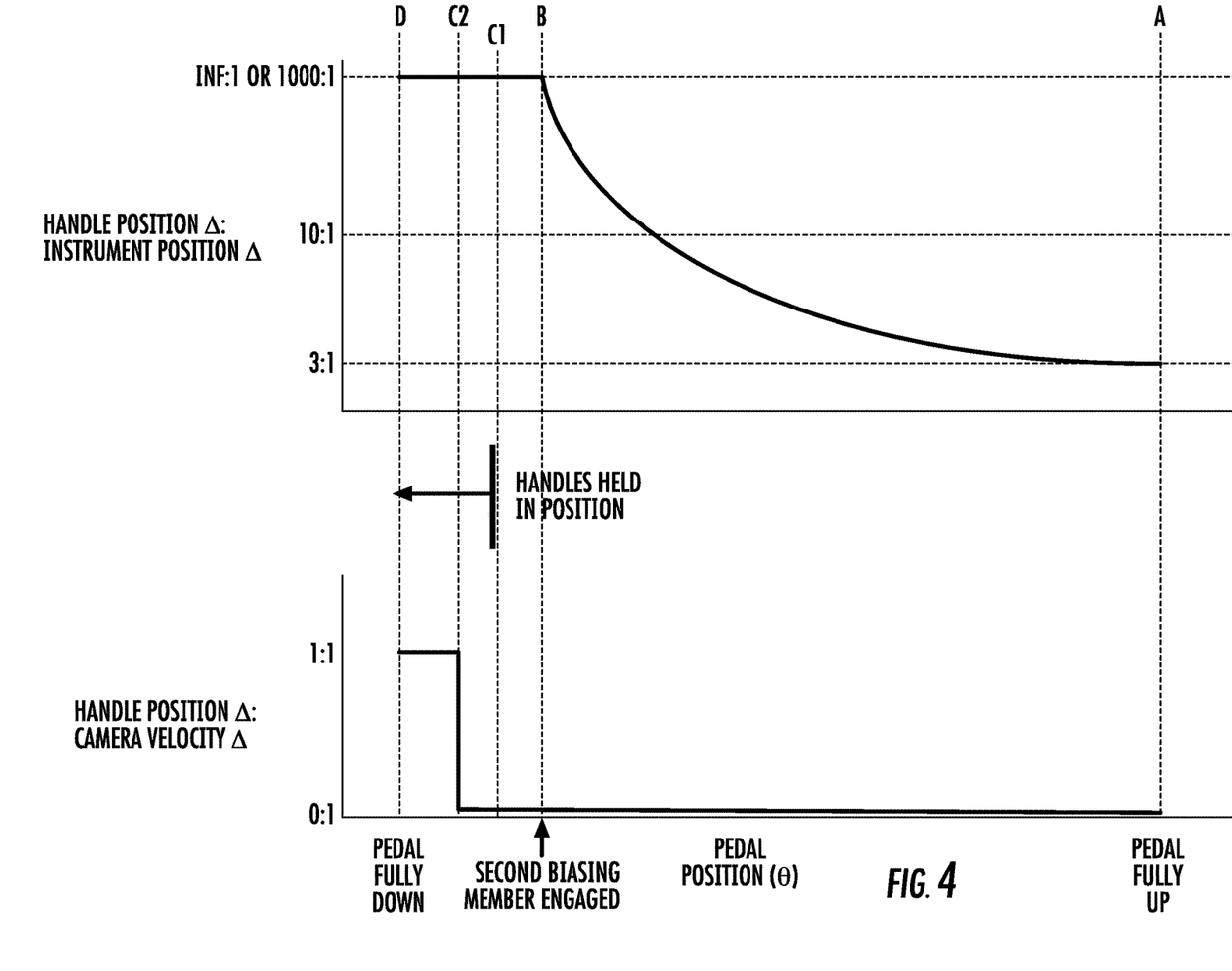
FIG. 4 are graphs illustrating another method of varying a scaling factor of an input handle of the user console of FIG. 1 to a tool of the surgical robot of FIG. 1 and a scaling factor of the input handle to a camera of the surgical robot of FIG. 1 based on a position of the foot pedal of FIG. 2.

With reference to FIG. 4, another method of using the foot pedal 60, to vary the scaling of the input handle 42 relative to the tool 20, and to vary a position of a camera, e.g., camera 56, in response to movement of the input handle 42, is disclosed with reference to the robotic surgical system 10 and foot pedal 60 of FIGS. 1-2D. Initially, as the foot pedal 60 is compressed towards the first compressed position, e.g., position "B", the scaling of movement of the input handle 42 to movement of the tool 20 varies as the foot pedal 60 is compressed from the 3:1 ratio at position "A" to a larger ratio, e.g., 1000:1 or infinite($\infty$):1, such that the input handle 42 is "clutched" or substantially "clutched" from movement of the tool when the foot pedal 60 is at or beyond the first compressed position. This also allows for a high precision mode as the foot pedal 60 approaches the first compressed position.

As the foot pedal 60 is compressed beyond the first compressed position, the foot pedal 60 engages the second biasing member 68. The input handle 42 may still move freely as the foot pedal 60 is compressed between the first compressed position and a second compressed position represented by "$C_1$". When the foot pedal 60 reaches the second compressed position, the input handle 42 enters a "hold mode" to define a "hold pose" of the input handle 42. When the input handle 42 is in the "hold mode", the control arm 43 may apply force feedback algorithms to the input handle 42 and/or the control arm 43 to maintain and/or return the input handle 42 to the hold pose.

As the foot pedal 60 is compressed beyond the second compressed position, the input handle 42 remains in the "hold mode" until foot pedal 60 reaches a third compressed position represented by "$C_2$". When the foot pedal 60 reaches the third compressed position, movement of the input handle 42 has little or no effect on movement of the tool 20 but moves the camera 23 within the surgical site "S" to adjust the view of the surgical site "S" on the display. The foot pedal 60 may include a third biasing member (not shown) that is engaged when the foot pedal 60 reaches the third compressed position to provide feedback to a user that the foot pedal 60 is at the third compressed position.

As detailed above, the foot pedal 60 can be used as both a clutch control and a camera control pedal. Providing a single foot pedal to act as both a clutch control and a camera control pedal may improve a user interface of a robotic surgical system. Specifically, the user interface may be improved by increasing the intuitiveness of the user interface, reducing the number of pedals, and/or decreasing the space required for the user interface. Improving the user interface may reduce the time and/or cost of robotic surgical procedures.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A robotic surgical system comprising:
   a surgical robot including a tool and a camera; and
   a user console in communication with the surgical robot, the user console including:
      an input handle; and
      a foot pedal including:
         a base plate; and
         a foot plate pivotally coupled to the base plate, the foot plate having:
            an uncompressed position in which movement of the input handle is scaled to movement of the tool by a first scaling factor,
            a first compressed position in which movement of the input handle is scaled to movement of the tool by a second scaling factor different from the first scaling factor,
            a second compressed position between the first compressed and fully compressed positions, and wherein movement of the input handle moves the camera when the foot plate is between the second compressed and fully compressed positions, and
            a fully compressed position in which movement of the input handle is scaled to movement of the camera.

2. The robotic surgical system according to claim 1, wherein the foot pedal includes a first biasing member configured to urge the foot plate towards the uncompressed position when the foot plate is between the fully compressed and uncompressed positions.

3. The robotic surgical system according to claim 2, wherein the foot pedal includes a second biasing member configured to urge the foot plate towards the uncompressed position when the foot plate is between the fully compressed and partially compressed positions.

4. The robotic surgical system according to claim 1, wherein the camera remains stationary in response to movement of the input handle when the foot pedal is between the uncompressed and first compressed positions.

5. The robotic surgical system according to claim 1, wherein between the first compressed and fully compressed positions the input handle is in a hold mode such that motors of the user console apply a force to the input handle to at least one of maintain or move the input handle to a hold pose.

6. The robotic surgical system according to claim 5, wherein the hold pose is defined by a pose of the input handle when the foot plate is compressed to the first compressed position.

7. The robotic surgical system according to claim 6, wherein the hold pose is redefined when the foot plate is moved from the first compressed position towards the uncompressed position and returned to the first compressed position.

8. The robotic surgical system according to claim 5, wherein the camera is throttled based on a distance the input handle is moved from the hold pose when the foot plate is in the fully compressed position.

9. The robotic surgical system according to claim 1, wherein the camera remains stationary in response to movement of the input handle when the foot plate is between the uncompressed and second compressed positions.

10. The robotic surgical system according to claim 1, wherein movement of the input handle is scaled to movement of the tool by a third scaling factor different from the first and second scaling factors when the foot plate is in the second compressed position.

11. The robotic surgical system according to claim 10, wherein movement of the input handle is scaled to movement of the tool by a fourth scaling factor different from the first, second, and third scaling factors when the foot plate is in the fully compressed position.

12. The robotic surgical system according to claim 11, wherein the first scaling factor is 3 and the second scaling factor is 10.

13. The robotic surgical system according to claim 11, wherein the third scaling factor is in a range of 11 to 500 and the fourth scaling factor is in a range of 100 to 1000.

14. A method of controlling a surgical robot with a processing unit of a robotic surgical system, the method comprising:
receiving a position of a foot pedal of a user console of the robotic surgical system;
receiving an input signal from the user console, the input signal including movement of an input handle of the user console; and
transmitting control signals to the surgical robot to move at least one of a tool of the surgical robot or a camera of the surgical robot in response to receiving the input signal,
wherein the processing unit scales:
the input signal to movement of the tool by a first scaling factor when the foot pedal is in an uncompressed position,
the input signal to movement of the tool by a second scaling factor different from the first scaling factor when the foot pedal is in a first compressed position,
the input signal to movement of the tool by a third scaling factor different from the first scaling factor or the second scaling factor when the foot pedal is in a second compressed position between the first compressed position and a fully compressed position, and
the input signal to movement of the camera when the foot pedal is in the fully compressed position.

15. The method according to claim 14, wherein the processing unit maintains the position of the camera when the foot pedal is between the uncompressed position and a second compressed position between the first compressed and fully compressed positions.

16. The method according to claim 14, wherein transmitting control signals to the surgical robot includes transmitting control signals to throttle movement of the camera when the foot pedal is between the second compressed and fully compressed positions.

17. A robotic surgical system comprising:
a surgical robot including a tool and a camera; and
a user console in communication with the surgical robot, the user console including:
an input handle; and
a foot pedal having:
an uncompressed position in which movement of the input handle is scaled to movement of the tool by a first scaling factor,
a first compressed position in which movement of the input handle is scaled to movement of the tool by a second scaling factor different from the first scaling factor,
a second compressed position between the first compressed and fully compressed positions, and wherein movement of the input handle moves the camera when the foot pedal is between the second compressed position and fully compressed position, and
a fully compressed position in which movement of the input handle is scaled to movement of the camera.

18. The robotic surgical system according to claim 17, wherein the camera remains stationary in response to movement of the input handle when the foot pedal is between the uncompressed and first compressed positions.

19. The robotic surgical system according to claim 17, wherein between the first compressed and fully compressed positions the input handle is in a hold mode such that motors of the user console apply a force to the input handle to at least one of maintain or move the input handle to a hold pose.

20. The robotic surgical system according to claim 19, wherein the hold pose is defined by a pose of the input handle when the foot pedal is compressed to the first compressed position.

21. The robotic surgical system according to claim 17, wherein the camera remains stationary in response to movement of the input handle when the foot pedal is between the uncompressed and second compressed positions.

22. The robotic surgical system according to claim 17, wherein movement of the input handle is scaled to movement of the tool by a third scaling factor different from the first and second scaling factors when the foot pedal is in the second compressed position.

23. The robotic surgical system according to claim 22, wherein movement of the input handle is scaled to movement of the tool by a fourth scaling factor different from the first, second, and third scaling factors when the foot pedal is in the fully compressed position.

* * * * *